US00PP35931P2

(12) United States Plant Patent
Strasko

(10) Patent No.: US PP35,931 P2
(45) Date of Patent: Jul. 2, 2024

(54) ***BAPTISIA* PLANT NAMED 'B247'**

(50) Latin Name: ***Baptisia* hybrid**
Varietal Denomination: B247

(71) Applicant: Ross Strasko, Lancaster, PA (US)

(72) Inventor: Ross Strasko, Lancaster, PA (US)

( * ) Notice: Subject to any disclaimer, the term of this patent is extended or adjusted under 35 U.S.C. 154(b) by 0 days.

(21) Appl. No.: 18/382,134

(22) Filed: Oct. 20, 2023

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP30,669 P3 * 7/2019 Hansen ..... A01H 5/02
Plt./263.1

* cited by examiner

*Primary Examiner* — Karen M Redden
(74) *Attorney, Agent, or Firm* — Penny J. Aguirre

(57) ABSTRACT

A new cultivar of hybrid *Baptisia* plant named 'B247' that is characterized by its flowers that open as a bright yellow in color and slowly change to purple as they mature, its upright plant habit with inflorescences that are held erect above the foliage, its dense foliar habit, its abundance of large size flowers, its sturdy and strong stems that do not flop in bloom, its stems that emerge purple in spring, and its mid-season blooming.

3 Drawing Sheets

Botanical classification: *Baptisi* hybrid.
Cultivar designation: 'B247'.

BACKGROUND OF THE INVENTION

The present invention relates to a new and distinct cultivar of *Baptisia* of hybrid origin and will be referred to hereinafter by its cultivar name, 'B247'. The new cultivar represents a new false indigo, an herbaceous perennial plant grown for ornamental landscape use.

The new cultivar was discovered as a chance seedling by the Inventor spring of 2021 in his nursery in Lancaster, Pennsylvania. The parents of the new cultivar are unknown, however *Baptisia* 'Solar Flare' (U.S. Plant Pat. No. 20,408) and *Baptisia* 'Lunar Eclipse' (U.S. Plant Pat. No. 25,875) are thought to be possible parents based on their proximity to the discovered seedling and the characteristics of the new cultivar.

Asexual propagation of the new cultivar was first accomplished by the Inventor by stem cuttings in 2022 in Lancaster, Pennsylvania. Asexual propagation by stem cuttings and tissue culture using meristematic tissue has determined the characteristics to be stable and reproduced true to type in successive generations.

SUMMARY OF THE INVENTION

The following traits have been repeatedly observed and are determined to be the characteristics of the new cultivar. These attributes in combination distinguish 'B247' as a unique cultivar of *Baptisia*.

1. 'B247' exhibits flowers that open as a bright yellow in color and slowly change to purple as they mature.
2. 'B247' exhibits an upright plant habit with inflorescences that are held erect above the foliage.
3. 'B247' exhibits a dense foliar habit.

4. 'B247' exhibits an abundance of large size flowers.
5. 'B247' exhibits sturdy and strong stems that do not flop in bloom.
6. 'B247' exhibits stems that emerge purple in spring.
7. 'B247' exhibits mid-season blooming.

The possible parent plant, 'Solar Flare', differs from 'B247' in having flowers that are bright yellow in color and mature to a red-brown color on the lower half of the inflorescences, flower color that changes more slowly, less flowers that are smaller in size and stems that emerge a dull purple-green color in spring and flop in bloom. The possible parent of 'B247', 'Lunar Eclipse', differs from 'B247' in having flowers that are white in color and change to purple, a very late blooming season, and foliage that is more blue-green in color. 'B247' can also be compared to the *Baptisia* cultivar 'Pink Lemonade' (U.S. Plant Pat. No. 30,669). 'Pink Lemonade' is similar to 'B247' in having yellow flowers that change to another color as they age. 'Pink Lemonade' differs from 'B247' in having paler yellow flowers that change to pink, a flower color transition that occurs on the bottom of the one-fourth of the inflorescence, and peduncles that are grey-green in color.

BRIEF DESCRIPTION OF THE DRAWINGS

The accompanying color photographs illustrate the overall appearance and distinct characteristics of a 4-year-old plant of the new *Baptisia* as grown outdoors in the ground in Leola, Pennsylvania.

The photograph in FIG. 1 provides a side view of a plant of 'B247' in bloom.

Figure 1:
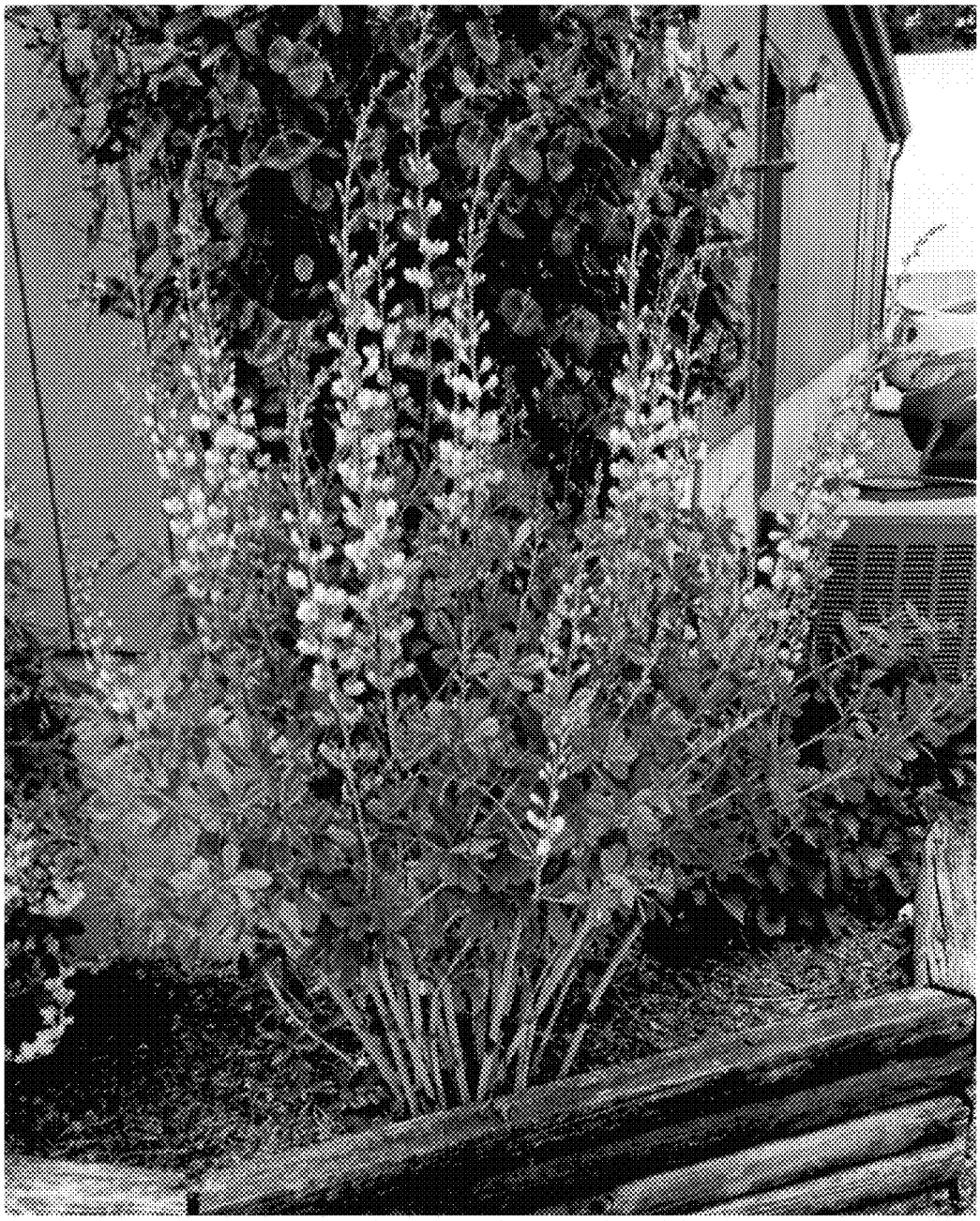
Figure 2:
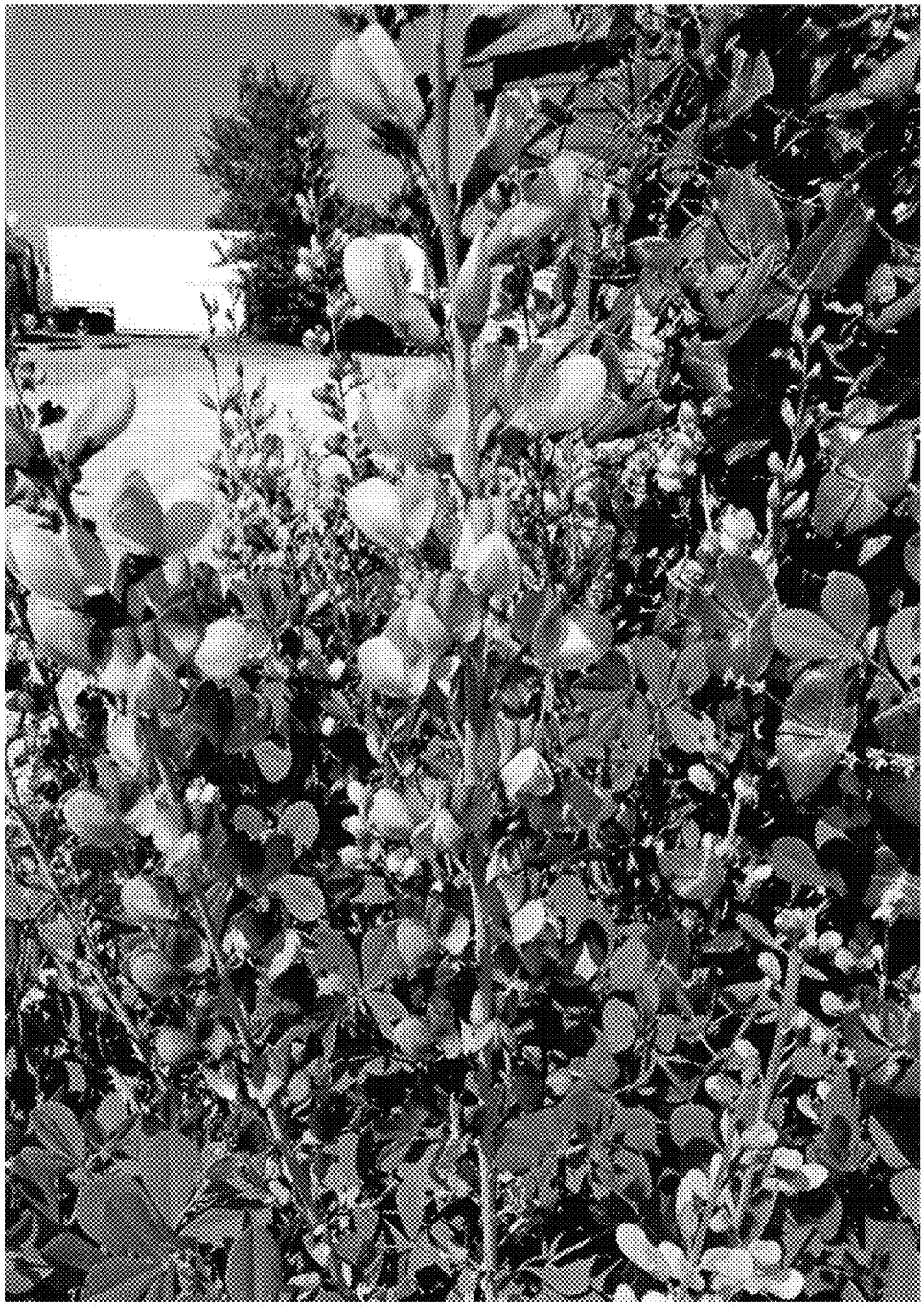

The photograph in FIG. 2 provides a close-up view of the inflorescences of 'B247'.

Figure 3:
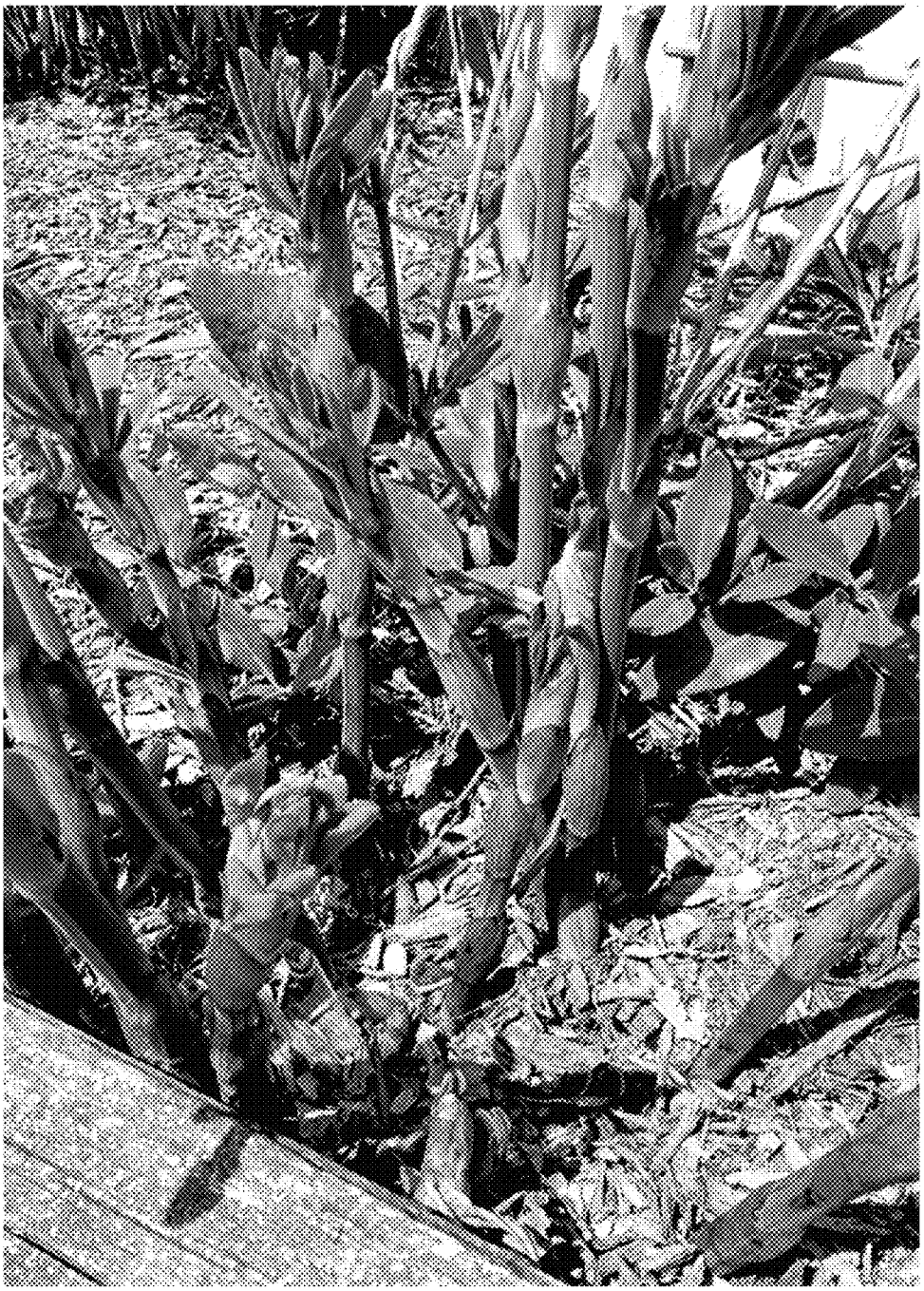

The photograph in FIG. 3 provides a close-up view of the emerging stems of 'B247'.

The colors in the photographs may differ slightly from the color values cited in the detailed botanical description, which accurately describe the colors of the new *Baptisia*.

DETAILED BOTANICAL DESCRIPTION

The following is a detailed description of the new cultivar as observed on 4-year-old plants of the new *Baptisia* as grown outdoors in the ground in Leola, Pennsylvania. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—3 weeks, late spring through early summer in Lancaster Pennsylvania.

*Plant type.*—Herbaceous perennial.

*Plant habit.*—Upright, dense foliage, strong stems that do not lodge.

*Height and spread.*—Reaches 1 to 1.2 m in height and an average of 1.2 m in spread as a 4-year-old plant in the landscape.

*Hardiness.*—At least in U.S.D.A. Zones 4 to 9.

*Diseases and pests.*—Some resistance to powdery mildew in autumn (caused by *Erysiphe* sp. or *Micosphaera* sp.) has been observed, no susceptibility or resistance to pests has been observed.

*Root description.*—Deep rooted, fibrous.

*Propagation.*—Stem cuttings and tissue culture.

*Time required for root development.*—An average of 8 to 10 weeks to produce a rooted plug from a stem cutting.

*Growth rate.*—Moderate.

Branch description:

*Branching habit.*—Well branched, average of 25 per plant.

*Branch size.*—Main stem; average of 82 cm (including peduncle) in length, 12 cm in length (excluding peduncle) and 5 mm in width (6 mm at base), secondary; average of 25 cm in length and 3 mm, tertiary; an average of 5 cm in length and 2 mm in width.

*Branch shape.*—Oval.

*Branch color.*—Emerging in spring; a blend of N187A and N187B, occasionally flushed with N81C, young and mature stems; 144A.

*Branch surface.*—Glabrous, satiny, slightly glossy, and slightly glaucous with vertical ridges.

*Branch strength.*—Main; strong, lateral; strong to moderately strong, tertiary; weak.

*Branch aspect.*—Main; vertical to slightly outward, lateral; held in a 50° angle from main branch, tertiary; held in a 20° angle from lateral branch.

Foliage description:

*Leaf shape.*—Fan-shaped in overall outline.

*Leaf division.*—3-palmate.

*Leaf size.*—Average of 7 cm in length and 10 cm in width.

*Leaflet size.*—An average of 6 cm in length and 2.5 cm in width (widest point).

*Leaf quantity.*—About 16 per stem.

*Leaflet shape.*—Oblanceolate.

*Leaflet base.*—Cuneate.

*Leaflet apex.*—Broadly acute and minutely retuse.

*Leaflet venation.*—Pinnate pattern, upper surface matches leaf surface, lower surface match leaf surface except main vein is 144A.

*Leaflet margins.*—Entire.

*Leaf attachment.*—Petiolate.

*Leaf arrangement. —Alternate.*

*Leaflet surface.*—Both surfaces glabrous, satiny, lower surface slightly glaucous.

*Leaflet color.*—Upper surface 137C, lower surface N138B.

*Leaf internode.*—Average of 2 cm, up to 14 cm.

*Petioles.*—Average of 1 cm in length and 2 mm in width, clasping to stem and slightly cupped under, 143C in color, surface is glabrous and glossy.

*Stipules.*—Narrowly lanceolate in shape, reflexed to stem, base is truncate to stem, apex is apiculate, average of 6 mm in length and 5 mm in width on mature leaves, 144A in color on both surfaces.

Flower description:

*Inflorescence type.*—Terminal racemes of pea-shaped flowers on main branch, blooms from the base to the apex.

*Inflorescence size.*—Average of 61 cm in length and 7 cm in width.

*Lastingness of inflorescences.*—3 to 4 weeks.

*Flower size.*—About 2.5 cm in depth and about 1.5 cm in diameter.

*Flower fragrance.*—None.

*Flower number per inflorescence.*—Average of 40 per plant.

*Peduncle.*—Oval in shape, up to 60 cm in length and an average of 5 mm in width, 143C to 143D in color, surface is glabrous, satiny and moderately glaucous, flower internode length averages about 1.5 cm.

*Pedicel.*—Average of 8 mm in length, about 1 mm in width, round in shape, 139D in color, glabrous and glossy surface.

*Flower buds.*—Kidney-shaped, average of 2.5 cm in length, 5 mm in width, color; emerging in spring; a blend of N187A and N187B, developed young buds 1A, before burst; 1B, lightly flushed with N187A.

*Flower type.*—Papilionaceous.

*Calyx.*—Campanulate, about 1 cm in depth and 6 mm in diameter, color; inner and outer surface 138A to 138B, inner surface glabrous and glossy, outer surface glabrous, matte, and slightly glaucous.

*Sepals.*—4, fused with the exception of apex of each, free portion is triangular in shape, 3 mm in width and 4 mm in depth with an acute and sometimes notched apex, color; inner and outer surface 138A to 138B, inner surface glabrous and glossy, outer surface glabrous, matte, and slightly glaucous, margins entire and densely covered with soft pubescent hairs, NN155B in color.

*Corolla features.*—Papilionaceous (4 segments) with a keel, a banner and 2 lateral wings, lateral wings; obelliptic in shape, slightly cupped, flared to expose keel, 2 cm in length and 1 cm in width, rounded apex, base is cuneate and fused, margins are entire and slightly undulate, both surfaces matte, satiny, very slightly rugose, color: when opening inner and outer surface 1B to 1C, base 11D, maturing half-way open inner and outer surface; top to mid-section a blend of N187A and 85A, base a blend of 1B and 11D, fully open and mature inner and outer surface; N187A and N92C, very bottom of base NN155D, slightly above bottom a section of 1B, keel; 2 segments surrounding reproductive organs, oblong (slightly oblique) in shape with rounded apex and narrow base that is slightly fused, 2 cm in length and 1 cm in width, margins are entire, both surfaces matte, satiny, very slightly rugose, color: when opening inner and outer surface; 1B and 1D, base 11D, maturing half-way open inner and outer surface; 2C, base NN155D, fully mature inner and outer surface; N187A to N187B, mid-section and base NN155D, flushed with 1C, banner; orbicular and kidney shaped, base and center fused, reflexed, 1.5 cm in length and 2 cm in width, apex is rounded, both surfaces matte and satiny, margins are entire and slightly undulate, color: when opening inner surface; outer edges 11C, center flushed with 6A and covered with a fountain shape of tiny dots that are 203A, when opening outer surface; 8A, lightly flushed with 1A, maturing half-way open inner surface; a blend of N187B and 4B, center flushed with 1C and covered with a fountain shape of tiny dots that are 203A, maturing half-way open outer surface; a blend of N187B and 4B, center flushed with 1C, fully mature inner surface; a blend of N187A to N187B, center lightly flushed with 2B and covered with a fountain shape of tiny dots that are N187A, fully mature outer surface; a blend of N187A to N187B, center lightly flushed with 2B.

*Receptacle.*—Disk-shaped, gelatinous, 140A in color, an average of 3 mm in diameter and 1.2 mm in depth.

Reproductive organs:

*Gynoecium.*—Pistil; 1 style; 8 mm in length, color; top to mid-section 3C, mid-section to base 143A, surface is glossy and glabrous, thick and round in shape, stigma; very minute, at the very tip of the style, NN155D in color, ovary; superior, flattened in shape, 140A and 141A in color, 1 cm in length and 2 mm in width.

*Androecium.*—Stamens; 10, filament; 2.3 cm in length, 1 mm in width, color; young a blend of 150D and 149D, mature NN155D, top becomes flushed with N187A, anther; dorsifixed, bifid and kidney shaped, 1 mm in length, 0.8 mm in diameter, color; young 21A, maturing to 10A, pollen; high in quantity and 21A in color.

*Fruit and seed.*—An inflated pod, average of 10 produced per inflorescence, globose-oblong to oval in shape, average of 3.5 cm in length, 1.5 cm in width, walls about 1 mm thick, woody and strong at maturity, slightly rugose and glabrous, matte surfaces, color; young inner and outer surface N144A, mature inner and outer surface a blend of N187A to N187B and N186A, seed; 4 to 10 per pod, kidney-shaped, surface is glabrous and slightly glossy, 4 mm in length, 3 mm in width, 1.3 mm in thickness, and 177B in color.

It is claimed:

1. A new and distinct cultivar of *Baptisia* plant named 'B247' as herein illustrated and described.

* * * * *